United States Patent
Scibona

(10) Patent No.: US 8,241,196 B2
(45) Date of Patent: Aug. 14, 2012

(54) BLOOD PROCESSING APPARATUS WITH DIGITALLY CONTROLLED LINEAR VOLTAGE REGULATOR FOR OPTICAL PULSES

(75) Inventor: Joseph A. Scibona, Littleton, CO (US)

(73) Assignee: Terumo BCT, Inc., Lakewood, CO (US)

( * ) Notice: Subject to any disclaimer, the term of this patent is extended or adjusted under 35 U.S.C. 154(b) by 293 days.

(21) Appl. No.: 12/631,289

(22) Filed: Dec. 4, 2009

(65) Prior Publication Data

US 2010/0160134 A1     Jun. 24, 2010

Related U.S. Application Data

(60) Provisional application No. 61/139,699, filed on Dec. 22, 2008.

(51) Int. Cl.
*B04B 15/00* (2006.01)
(52) U.S. Cl. ............................................ 494/10; 494/43
(58) Field of Classification Search ................... 494/10, 494/43, 37, 45; 210/782; 604/6.08
See application file for complete search history.

(56) References Cited

U.S. PATENT DOCUMENTS

| | | | |
|---|---|---|---|
| 3,955,755 A | 5/1976 | Breillatt et al. |
| 4,151,844 A | 5/1979 | Cullis et al. |
| 4,493,691 A | 1/1985 | Calari |
| 4,557,719 A | 12/1985 | Neuman et al. |
| 4,670,002 A | 6/1987 | Koreeda et al. |
| 4,671,102 A | 6/1987 | Vinegar et al. |
| 4,724,317 A | 2/1988 | Brown et al. |
| 4,834,890 A | 5/1989 | Brown et al. |
| 4,936,820 A | 6/1990 | Dennehey et al. |
| 5,076,911 A | 12/1991 | Brown et al. |
| 5,104,526 A | 4/1992 | Brown et al. |
| 5,260,598 A | 11/1993 | Brass et al. |
| 5,316,667 A | 5/1994 | Brown et al. |
| 5,322,620 A | 6/1994 | Brown et al. |
| 5,653,887 A | 8/1997 | Wahl et al. |
| 5,814,279 A | 9/1998 | Biesel et al. |
| 5,930,033 A | 7/1999 | Inove et al. |

(Continued)

FOREIGN PATENT DOCUMENTS

DE          3413065          10/1984

(Continued)

OTHER PUBLICATIONS

International Search Report for PCT/US2009/066792, filed Dec. 4, 2009 and mailed Jun. 15, 2010.

(Continued)

*Primary Examiner* — Walter D Griffin
*Assistant Examiner* — Timothy Cleveland
(74) *Attorney, Agent, or Firm* — John R. Merkling; Elizabeth J. Reagan; René A. Pereyra

(57) ABSTRACT

The invention relates to apparatus for controlling the processing of blood into blood components, particularly components for stroboscopic LED light sources for centrifuges. A digital control circuit controls a high amperage linear voltage regulator. The voltage regulator charges a capacitor bank, which in turn powers LED light sources. The digital control circuit comprises an N-channel switched mode FET. The switched mode FET receives a pulsed digital signal from the microprocessor controlling the blood processing apparatus. A by-pass resistor in parallel with the FET allows most of the current to flow past the FET, thus minimizes heating of the FET. The performance of the FET, therefore, remains stable despite extended use of the apparatus.

17 Claims, 8 Drawing Sheets

U.S. PATENT DOCUMENTS

| | | | |
|---|---|---|---|
| 5,948,271 | A | 9/1999 | Wardwell et al. |
| 6,053,856 | A | 4/2000 | Hlavinka |
| 6,334,842 | B1 | 1/2002 | Hlavinka et al. |
| 6,338,820 | B1 | 1/2002 | Hubbard et al. |
| 6,506,606 | B1 | 1/2003 | Winkelman et al. |
| 6,514,189 | B1 | 2/2003 | Hlavinka et al. |
| 6,632,399 | B1 | 10/2003 | Kellogg et al. |
| 6,790,371 | B2 | 9/2004 | Dolecek |
| 7,327,443 | B2 | 2/2008 | Scibona et al. |
| 2002/0147094 | A1 | 10/2002 | Dolecek |
| 2002/0196435 | A1 | 12/2002 | Cohen et al. |
| 2006/0001860 | A1 | 1/2006 | Scibona et al. |
| 2007/0085996 | A1* | 4/2007 | Mangan et al. ............. 494/10 |

FOREIGN PATENT DOCUMENTS

| | | |
|---|---|---|
| EP | 0392475 | 10/1990 |
| JP | 4371245 | 12/1992 |
| WO | WO2008/079583 | 7/2008 |

OTHER PUBLICATIONS

Partial International Search Report for PCT/US2009/066792, filed Dec. 4, 2009 and mailed Apr. 15, 2010.

Salgaller, Michael L., "A Manifesto on the Current State of Dendric Cells in Adoptive Immunotherapy", *Transfusion*, 2003, 43(4):422-424.

* cited by examiner

BLOOD PROCESSING APPARATUS WITH DIGITALLY CONTROLLED LINEAR VOLTAGE REGULATOR FOR OPTICAL PULSES

CROSS-REFERENCE TO RELATED APPLICATIONS

This application claims the benefit of U.S. Provisional Application 61/139,699, filed Dec. 22, 2008.

BACKGROUND OF INVENTION

This application is related to U.S. Pat. Nos. 7,422,693 and 7,327,443, which are hereby incorporated by reference in their entirety to the extent not inconsistent with the disclosure herein.

Blood collection and processing play important roles in the worldwide health care system. In conventional blood collection, blood is removed from a donor or patient, separated into its various blood components via centrifugation, filtration and/or elutriation and stored in sterile containers for future infusion into a patient for therapeutic use. Apheresis blood collection techniques have also been adopted in many blood collection centers wherein a selected component of blood is collected and the balance of the blood is returned to the donor during collection. An advantage of this method is that it allows more frequent donation from an individual donor because only a selected blood component is collected and purified.

Apheresis blood processing also plays an important role in a large number of therapeutic procedures. In these methods, blood is withdrawn from a patient undergoing therapy, separated, and a selected fraction is collected while the remainder is returned to the patient. For example, a patient may undergo leukapheresis prior to radiation therapy, whereby the white blood cell component of his blood is separated, collected and stored to avoid exposure to radiation. Further, apheresis may be used to perform therapeutic platelet depletion for patients having thrombocytosis and therapeutic plasma exchange for patients with autoimmune diseases.

Both conventional blood collection and apheresis systems typically employ differential centrifugation methods for separating blood into its various blood components. In differential centrifugation, blood is circulated through a sterile separation chamber, which is rotated at high rotational speeds about a central rotation axis. The centrifugal force generated upon rotation separates particles suspended in the blood sample into discrete fractions having different densities. Descriptions of blood centrifugation devices are provided in U.S. Pat. No. 5,653,887 and U.S. Pat. No. 7,033,512.

To achieve continuous, high throughput blood separation, extraction or collection ports are provided in most separation chambers. Extraction ports are disposed at selected positions along the separation axis corresponding to discrete blood components. To ensure the extracted fluid exiting a selected extraction port is substantially limited to a single phase, however, the phase boundaries between the separated blood components must be positioned along the separation axis such that an extraction port contacts a single phase, such as platelet enriched plasma, white blood cells, or red blood cells.

The purity of extracted blood components using density centrifugation is currently limited by the control of the position of phase boundary layers between separated components. Given the sensitivity of the phase boundary position to many variables, which change from person to person and during processing, it is important to monitor the position of the phase boundaries during blood processing to ensure optimal separation conditions are maintained and the desired purity of selected blood components is achieved. In addition, accurate characterization of the positions of phase boundaries allows for separation conditions to be adjusted and optimized for changes in blood composition during processing.

It will be appreciated from the foregoing that a need exists for methods and devices for monitoring and controlling the processing of whole blood samples and blood component samples. Particularly, optical monitoring methods and devices are needed which are capable of accurately characterizing the separation, extraction and collection of blood components processed by density centrifugation, including providing controlled stroboscopic light sources with consistent duration and intensity of illumination.

SUMMARY OF THE INVENTION

This invention provides a digitally controlled voltage regulator for a stroboscopic LED light source for use with devices for improving the processing of fluids, such as blood, components of blood and fluids derived from blood.

An exemplary optical monitoring system for a density centrifuge having a separation chamber rotating about a central rotation axis comprises at least one light source, a light collection element and a detector. Rotation of the separation chamber about a central rotation axis results in separation of the blood components in the separation chamber according to density. Both the light source and light collection element are arranged such that they are periodically in optical communication with an observation region on the density centrifuge.

The blood processing apparatus described herein uses precisely controlled pulses of light to illuminate blood components in the observation region, detect the state of separation of the blood components, and control the operation of the blood processing apparatus. A wide range of light intensities is needed to accommodate a wide range of blood processing procedures. In addition to pulse duration, control may be accomplished by voltage control of voltages applied to the light sources. Moreover, the control should be temperature independent, and stable over the expected operating temperatures of the blood processing device.

A digital control circuit is described herein for controlling a high amperage linear voltage regulator. The voltage regulator charges a capacitor bank, which in turn powers LED light sources. The digital control circuit comprises an N-channel switched mode FET. The switched mode FET receives a pulsed digital signal from the microprocessor controlling the blood processing apparatus. A by-pass resistor in parallel with the FET allows most of the current to flow past the FET, thus minimizing heating of the FET. The performance of the FET, therefore, remains stable despite extended use of the apparatus.

The pulsed output of the FET is coupled in parallel across a smoothing capacitor. In this manner, a selected voltage drop is maintained which is dependent on the switching rate and pulse width of the FET, but which is seen by the voltage regulator as a constant selected voltage.

The control circuit described herein allows for temperature-stable control of the voltage regulator and capacitor bank over a relatively wide range of selected voltages, for example between 3 volts and 22.5 volts. Moreover, the voltage stored on the capacitor bank can be precisely controlled within 0.1 volts or less despite high amperage output from the voltage regulator to the capacitor bank, thus allowing precise control of the LED light sources over a wide range of power levels. Over two hundred set points may be provided over the voltage range without the use of additional feedback (which could interact with internal feedback controls built into integrated linear voltage regulators) and without the use of additional temperature compensation circuits. These features allow the blood processing apparatus to be programmed for numerous blood processing procedures without re-calibrating the LED light sources.

An aspect of the invention is to provide a centrifuge blood processing system for separating blood components comprising a separation chamber rotating about a central axis, the separation chamber having an observation region; a stroboscopic light source illuminating the observation region; a camera receiving images of the observation region; an intensity control apparatus, the intensity control apparatus having at least one capacitor coupled to the light source, a linear voltage regulator coupled to and periodically charging the capacitor, and means for digitally controlling the output voltage of the linear voltage regulator. The stroboscopic light source may comprise light emitting diodes (LED).

In another aspect of the invention the means for digitally controlling the output voltage may be a switched mode field effect transistor (FET).

Yet another feature of the invention may include a microprocessor and means for controlling the switched mode FET with a pulsed digital signal from the microprocessor. It is also an aspect of the invention to provide a by-pass resistor in parallel with the FET.

A smoothing capacitor may also be connected to the FET, the smoothing capacitor converting pulsed output of the FET into a stable output for controlling the linear voltage regulator. In addition, a high-frequency by-pass capacitor may be coupled to the FET.

Another feature of the invention may include an intensity control apparatus having at least one capacitor coupled to the light source, a linear voltage regulator coupled to and periodically charging the capacitor, and a digital control circuit controlling the output voltage of the linear voltage regulator.

Another object of the invention may be to provide means for digitally controlling voltage delivered to the light source up to at least 22.5 volts in increments of 0.1 volts or less.

Yet another aspect of the invention may include means for controlling voltage delivered to the stroboscopic light source, the means for controlling voltage being temperature independent, and stable over the expected operating temperatures of the blood processing device.

Additional advantages include the possibility of automated calibration and diagnostics by digital control of programmed pulse generation coupled with optical feedback in the system.

These and other features and advantages of the invention will be apparent from the following description of the invention, together with the accompanying drawings. The invention is therefore further illustrated by the following description, examples, drawings and claims.

DETAILED DESCRIPTION OF THE INVENTION

Figure 1:
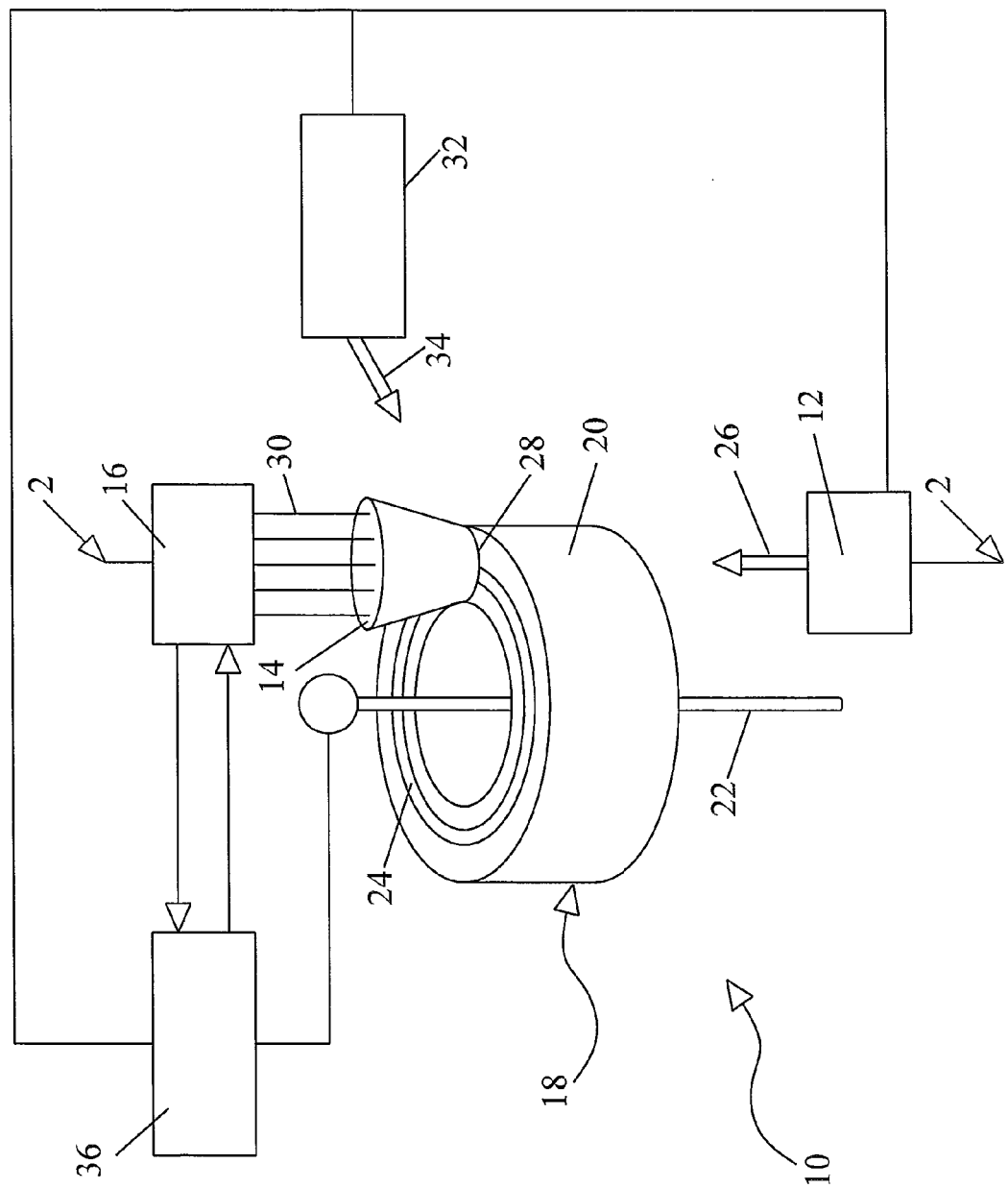
FIG. 1 is a schematic drawing showing an optical monitoring and control system of the present invention.

Referring to the drawings, like numerals indicate like elements and the same number appearing in more than one drawing refers to the same element.

FIG. 1 schematically illustrates an exemplary embodiment of an optically monitored blood processing system 10. The illustrated blood processing system 10 comprises stroboscopic light source 12, light collection element 14, and detector 16. Stroboscopic light source 12 is in optical communication with a density centrifuge 18 comprising a rotor 20, which rotates about central rotation axis 22. Rotation about central rotation axis 22 results in separation of a blood sample in a separation chamber 24 into discrete blood components. The rotor 20 has an internal, circular groove wherein the separation chamber 24 is positioned and fastened. During operation of the density centrifuge, the rotor 20 is operationally connected to a rotating means such that both rotor 20 and separation chamber 24 are rotated about the central rotation axis 22. The blood sample is separated into an outer higher density phase corresponding to a red blood cell component, an intermediate density phase corresponding to a white blood cell and platelet-containing component (e.g. buffy coat), and a lower density inner phase corresponding to a platelet enriched plasma component.

Light source 12 provides an incident light beam 26, which illuminates an observation region 28 on separation chamber 24. In one embodiment, a portion of the incident light beam is transmitted through at least one blood component undergoing separation in separation chamber 24. At least a portion of the light 30 from the observation region 28 is collected by light collection element 14. Light collection element 14 directs at least a portion of the collected light 30 onto detector 16. The detector 16 detects patterns of light 30 from the observation region 28.

In the exemplary embodiment illustrated in FIG. 1, separated blood components and phase boundaries between optically differentiable blood components are viewable in observation region 28. In one embodiment, the observation region is positioned on an optical cell of the separation chamber having windows for transmitting the incident beam through the blood sample undergoing processing. In an alternative embodiment, one or more extraction ports (not shown in FIG. 1) are viewable in observation region 28. In another embodiment, the observation region 28 is positioned on a portion of the separation chamber such that the composition of a separated blood component can be directly monitored.

Optionally, the observation region 28 can also be illuminated by stroboscopic light source 32, which is positioned on the same side of the separation chamber as the light collection element and detector. Stroboscopic light source 32 generates an incident beam 34, a portion of which is collected by light collection element 14 and detected by detector 16.

In the exemplary embodiment shown in FIG. 1, detector 16 is operationally connected to a centrifugation device controller 36 capable of receiving the output signals. In one embodiment, centrifugation device controller 36 displays the measured intensity distributions, stores the measured intensity distributions, processes measured intensity distributions in real time, transmits control signals to various optical and mechanical components of the monitoring system and centrifuge or any combination of these. In a preferred embodiment, centrifugation device controller 36 is operationally connected to centrifuge 18 and is capable of adjusting selected operating conditions of the density centrifuge, such as the flow rates of cellular and non-cellular components out of the separation chamber, the position of one or more phase boundaries along the separation axes, rotational velocity of the separation chamber about central rotation axis 22, the infusion of anticoagulation agents or other blood processing agents to the blood sample, or any combination of these.

As shown in FIG. 1, centrifugation device controller 36 can also be operationally connected to light source 12 or light source 32. In this embodiment, centrifugation device controller 36 or detector 16 are capable of generating output signals for controlling illumination conditions. For example, output signals from detector 16 can be used to control the timing of illumination pulses, illumination intensities, the distribution of illumination wavelengths, or the positions of the light sources 12, 32. Centrifugation device controller and detector are in two-way communication. In this embodiment, centrifuge device controller sends control signals to detector 16 to selectively adjust detector exposure time, detector gain and to switch between monochrome and color imaging.

Light sources of the present invention comprise light emitting diode sources capable of generating one or more incident beams for illuminating the observation region on the density centrifuge. A plurality of lamps may be positioned to illuminate a single side or multiple sides of a density centrifuge. Light sources useable in the present invention include light emitting diodes and arrays of light emitting diode light sources. Use of light emitting diode light sources is preferred for some applications because they are capable of generating precisely timed illumination pulses. Preferred light sources generate an incident light beam having a substantially uniform intensity. Light sources may generate an incident beam having a selected wavelength range and selected intensity.

Figure 2:
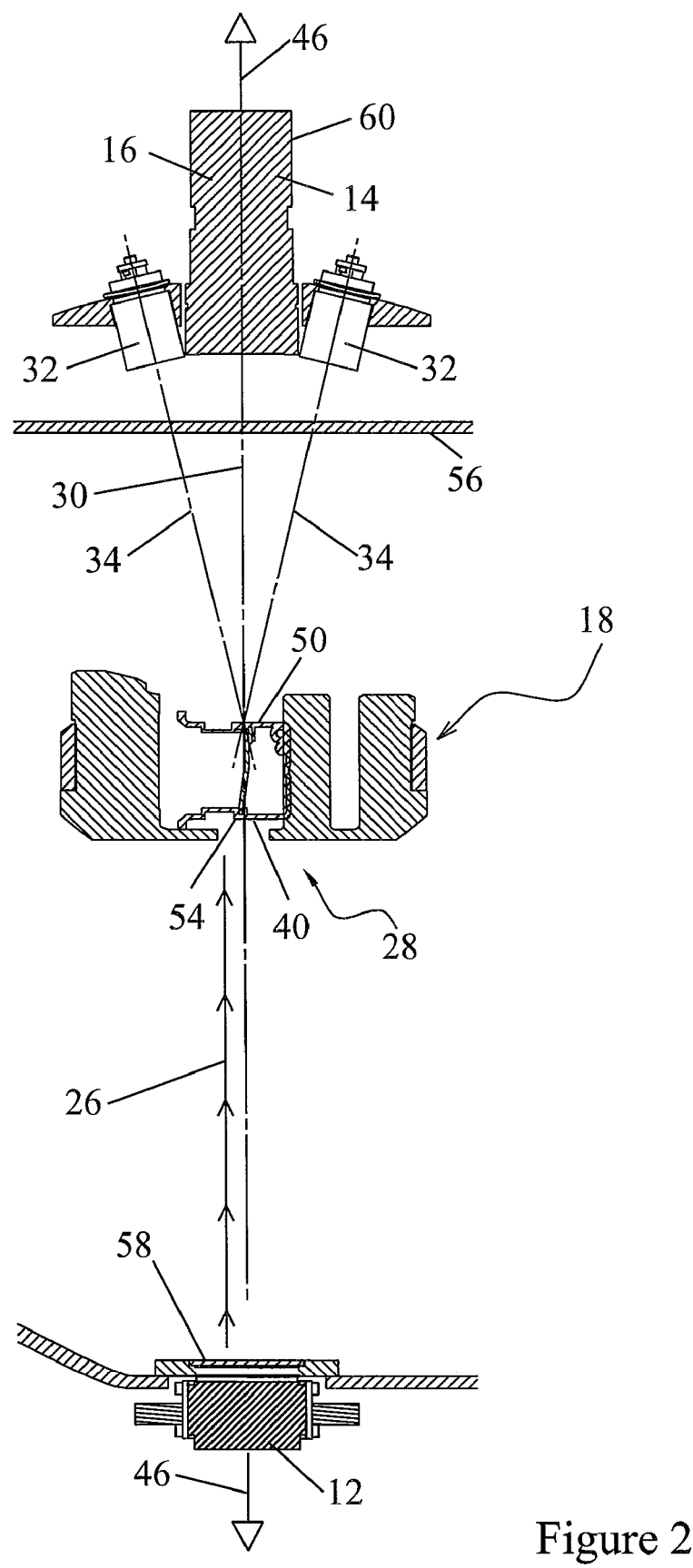
FIG. 2 is a cross sectional view corresponding to cut away line 2-2 indicated in FIG. 1.
Figure 3:
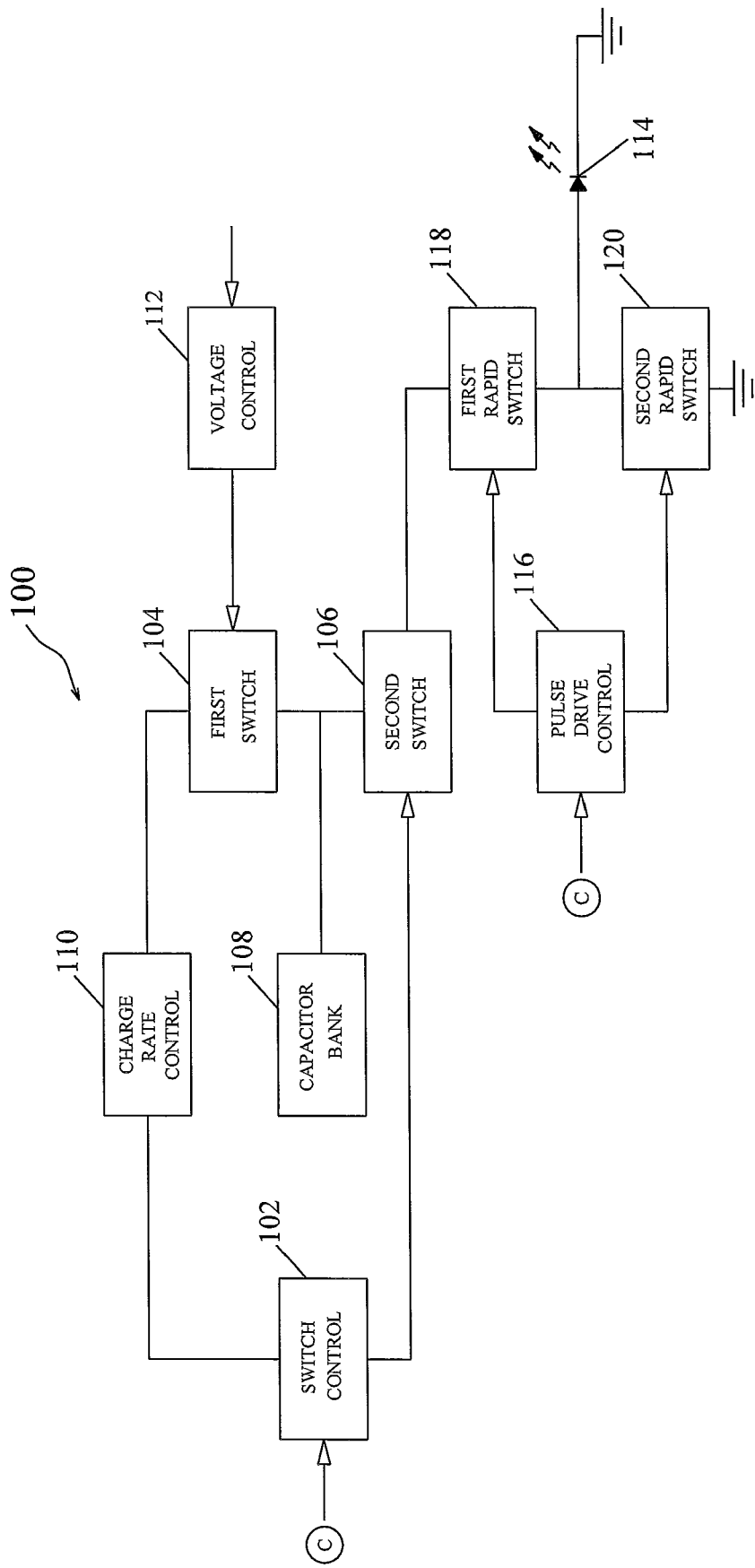
FIG. 3 is a functional block diagram of a control circuit.

FIG. 2 is a cross sectional view corresponding to cut away line 2-2 indicated in FIG. 1. The illustrated optical monitoring and control system comprises the detector 16 which may be a CCD camera and the light collection element 14 which may be a fixed focus lens system, an optical cell 40 in the observation region 28, a top pulsed LED light source 32, and a bottom pulsed LED light source 12. As illustrated in FIG. 3, CCD camera detector 16 is in optical communication with optical cell 40 and positioned to intersect optical axis 46. Top pulsed LED light source 32 is in optical communication with optical cell 40 and is positioned such that it is capable of directing a plurality of light beams 34, propagating along propagation axes that intersect optical axis 46, onto the top side 50 of optical cell 40. Bottom pulsed LED light source 12 is also in optical communication with optical cell 40 and directs one or more light beams 26, onto the bottom side 54 of optical cell 40.

Referring to the cross section shown in FIG. 2, first transparent plate 56 is provided between CCD camera detector 16 and optical cell 40, and second transparent plate 58 is provided between bottom pulsed LED light source 12 and optical cell 40. First and second transparent plates 56 and 58 physically isolate CCD camera detector 16, top pulsed LED light source 32 and bottom pulsed LED light source 12 from optical cell 40 so that these components will not contact a sample undergoing processing in the event of sample leakage from the separation chamber.

Top pulsed LED light source 32 and bottom pulsed LED light source 12 are capable of providing synchronized light pulses having accurately selectable temporal characteristics. Pulse widths of light pulses useable in the present invention depend on the rotational velocity of the density centrifuge. Typically, the smaller the pulse width of the light pulse, the less blurring of the optical image corresponding to the acquired distribution of light intensities. However, larger pulse widths allow more photons to be integrated by the CCD of the camera and, thus, provide enhanced signal-to-noise ratios. For a rotational velocity equal to about 3000 RPM, pulse widths less than about 8 microseconds are useful for minimizing blurring of the image of the optical cell generated. Exemplary light pulses useful for some applications of the present invention have pulse widths selected over the range of about 1 microsecond to about 50 microseconds.

In one embodiment, CCD camera detector 16 comprises a monochrome or color CCD camera positioned a fixed, selected distance from a fixed focus lens system. CCD camera and fixed focus lens system can be contained in a housing 60 capable of maintaining the selected separation distance between these elements and also capable of minimizing detection of unwanted scattered light. An exemplary CCD camera is the "Flea" manufactured by Point Grey Research, Inc. and has a pixel area equal to about 1024 pixels by 768 pixels. An exemplary lens comprises an F 2.8 fixed focal length lens system having a focal length of 28 millimeters manufactured by Schneider Optics, Inc.

Light 30 transmitted and/or scattered by optical cell 40 is collected by fixed focal length lens system and imaged onto the sensing surface of the CCD camera. In this manner, a distribution of light intensities is measured by CCD camera that corresponds to an image of at least a portion of optical cell 40. Detection of scattered light corresponding to the upper illumination light beams 34 is primarily used for system calibration, proximity identification and translational sensor tracking. Detection of transmitted light corresponding to the bottom illumination light beams 26 is primarily used for measurement of the position of one or more phase boundary layers of optically differentiable separated blood components in optical cell 40 and for measurement of the composition and flux of separated blood components exiting one or more extraction ports of optical cell 40. Detecting transmitted and scattered light arising from both top and bottom illumination maximizes the amount of information that can be extracted from an acquired distribution of light intensities and enhances the multifunctional capabilities of optical monitoring and control systems of the present invention.

The CCD camera is capable of generating one or more output signals, corresponding to the measured distribution of light intensities. Output signals are sent to one or more centrifuge device controllers 36, such as a computer or processor, capable of analyzing the acquired distributions of transmitted and/or scattered light intensities and adjusting important operating conditions which affect separation conditions and the composition of extracted blood components. Selectively adjustable operating conditions include, but are not limited to, the rotational velocity of the centrifuge, the flow rates of one or more inlet pumps, and the flow rates of one or more extraction pumps, or any combination of these.

In an exemplary embodiment, the exposure time of the CCD camera is determined by the pulse width of the light pulses generated by the top and bottom pulsed LED light sources, rather than by the gating setting or shutter of the CCD camera. In one embodiment, the shutter of the CCD camera can be opened longer than the light pulse duration without having significant background noise affects. As the pulse widths of light pulses generated by LED light sources can be controlled very accurately, this aspect of the present invention eliminates the need of costly CCD cameras providing very accurate gating corresponding to short exposure times.

In a preferred embodiment, each of the LED light sources are controlled by control circuits, such as control circuit 100, illustrated in functional block diagram in FIG. 3. A control circuit 100 may control all or any subset of the LED light sources. Preferably, however, a single control circuit controls two LED devices having the same frequency characteristics and positioned so that the failure of one LED device would not significantly affect the function of the apparatus as a whole. The control circuit 100 comprises a switch control unit 102 that selectively opens and closes a first switch circuit 104 and a second switch circuit 106 in response to signals from a microprocessor to maintain a selected charge on a bank 108 of power capacitors. The first switch circuit 104 is initially closed to charge the capacitor bank 108 while the second switch circuit 106 is open. A charging rate control circuit 110 limits the rate at which charge can be transferred to the capacitor bank 108. This prevents a sudden current demand as the system is initialized. Such a sudden demand might interfere with other power demands of the system as a whole. The charging rate may be fixed and not programmable, while other parameters of the control circuit 100 are programmable. The charging rate could be made programmable by using the digital potentiometer that adjusts the voltage stored on the capacitor bank 108. The microprocessor could then control charging by ramping the setting of the digital potentiometer at the programmed, controlled rate of change.

A novel digitally controlled voltage control circuit 112 regulates the peak voltage stored on the capacitor bank 108. This circuit will be described more fully below. The microprocessor selects the voltage stored on the capacitor bank 108 and preferably adjusts a digitally controllable device in the voltage control circuit. After the capacitor bank 108 is charged to its selected voltage, first switch circuit 104 can be left closed, allowing charging to continue during normal operation, and second switch circuit 106 can be closed, providing driving power to the LED devices through other circuit components, as explained below. The switch control unit 102 provides timing and control signals to close the first switch circuit 104 and to close the second switch circuit 106. When both switch circuits 104 and 106 are closed, power is established within the capacitor bank 108.

With second switch circuit 106 closed, power is available to the LED device or devices 114. Responsive to signals from the microprocessor, a pulse drive controller 116 controls first rapid response switch 118 and second rapid response switch 120, which bracket the LED device 114. Each of the rapid response switches 118, 120 is configured to turn on or off in such a manner to provide a well-defined square power wave to the LED device 114. With the second rapid response switch open, the first response switch can be closed to provide a path for current from the capacitor bank 108 through the LED device 114 to ground. As will be explained more fully below, the leading edge of the wave is well defined and abrupt and the voltage then remains relatively constant because of the substantial size of the capacitors in the capacitor bank 108. After the selected illumination period, the pulse drive controller 116 briefly turns off both switches 118, 120, as explained above in connection with the first and second switch circuits 104, 106, and then opens the second rapid response switch 120 to ground, draining any remaining power away from the LED device 114, and sharply and precisely turning the LED device 114 off.

The control circuit 100 produces a precisely controlled stroboscopic illumination. Both the duration and the magnitude (voltage) of the LED device output can be digitally controlled. This contrasts with xenon stroboscopic flash tubes, where the light-generating phenomenon is essentially an explosion, with an uncertain duration and an indeterminate intensity. In the preferred application for the present stroboscopic light, the target image is relatively far both from the light source and the detection device (video camera), but the phenomenon being detected, a boundary between fluid layers, is quite subtle. An intense yet consistent illumination is needed. Because the shutter speed of the camera is slower that the phenomenon being observed, the stroboscopic flash serves as the shutter for the optical system, and must, therefore, have both an abrupt beginning and end. These features are provided by the LED light sources and control circuits described herein.

Moreover, in the preferred application of the stroboscopic light, the limiting parameter tends to be the refresh rate for the video camera, which is generally limited to about 25-30 Hz, that is, one image for every second revolution of the rotor. Because this cycle between images is relatively long compared to the period of illumination by the LED light sources, the control circuit 100 has ample time to fully recharge the capacitor bank 108 through first and second switch circuits 104, 106 before power is supplied to the LED device 114 through first and second rapid response switches 118, 120.

Figure 4:
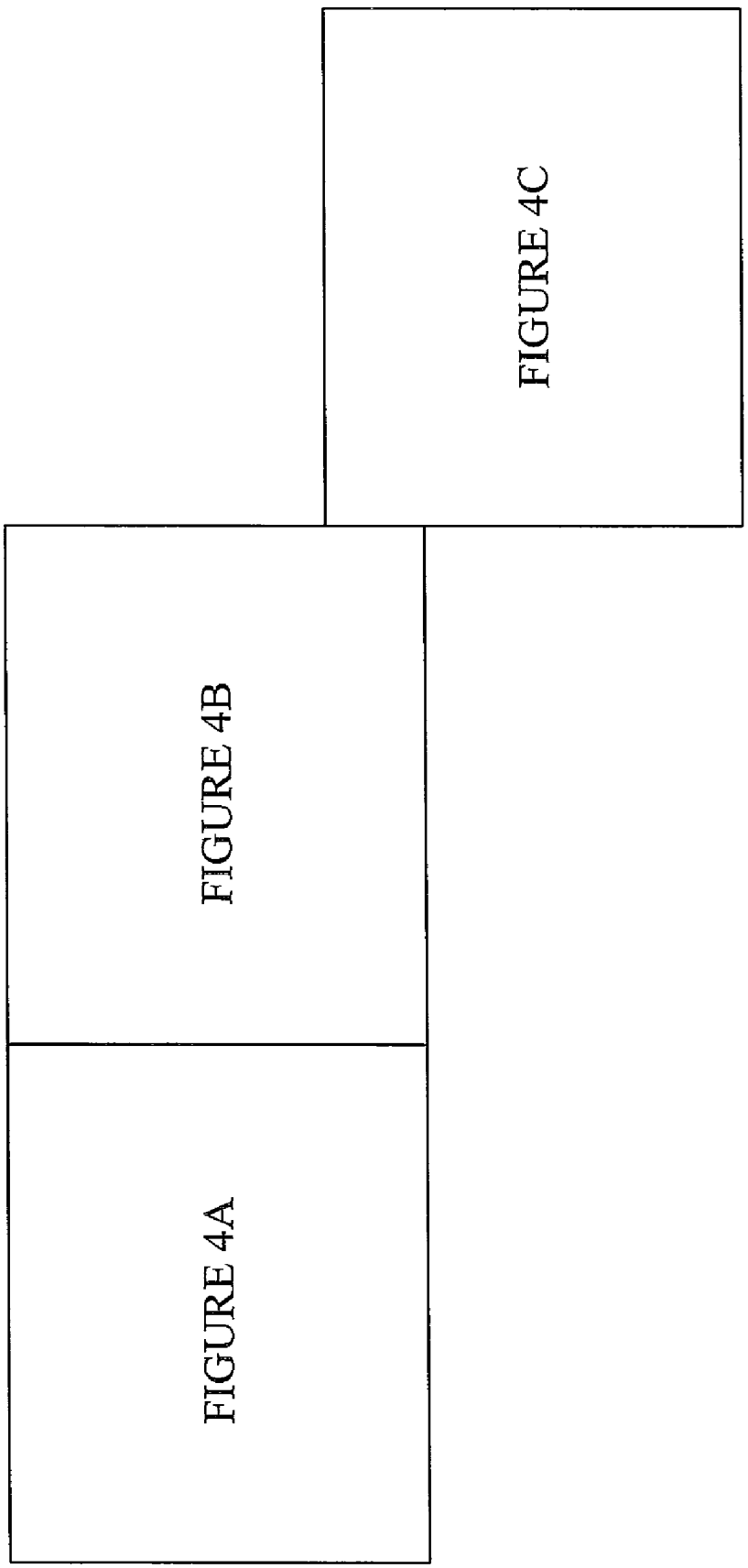
FIG. 4 shows the relationship of FIGS. 4A, 4B and 4C, which are schematic diagrams of the control circuit of FIG. 3.
Figure 4A:
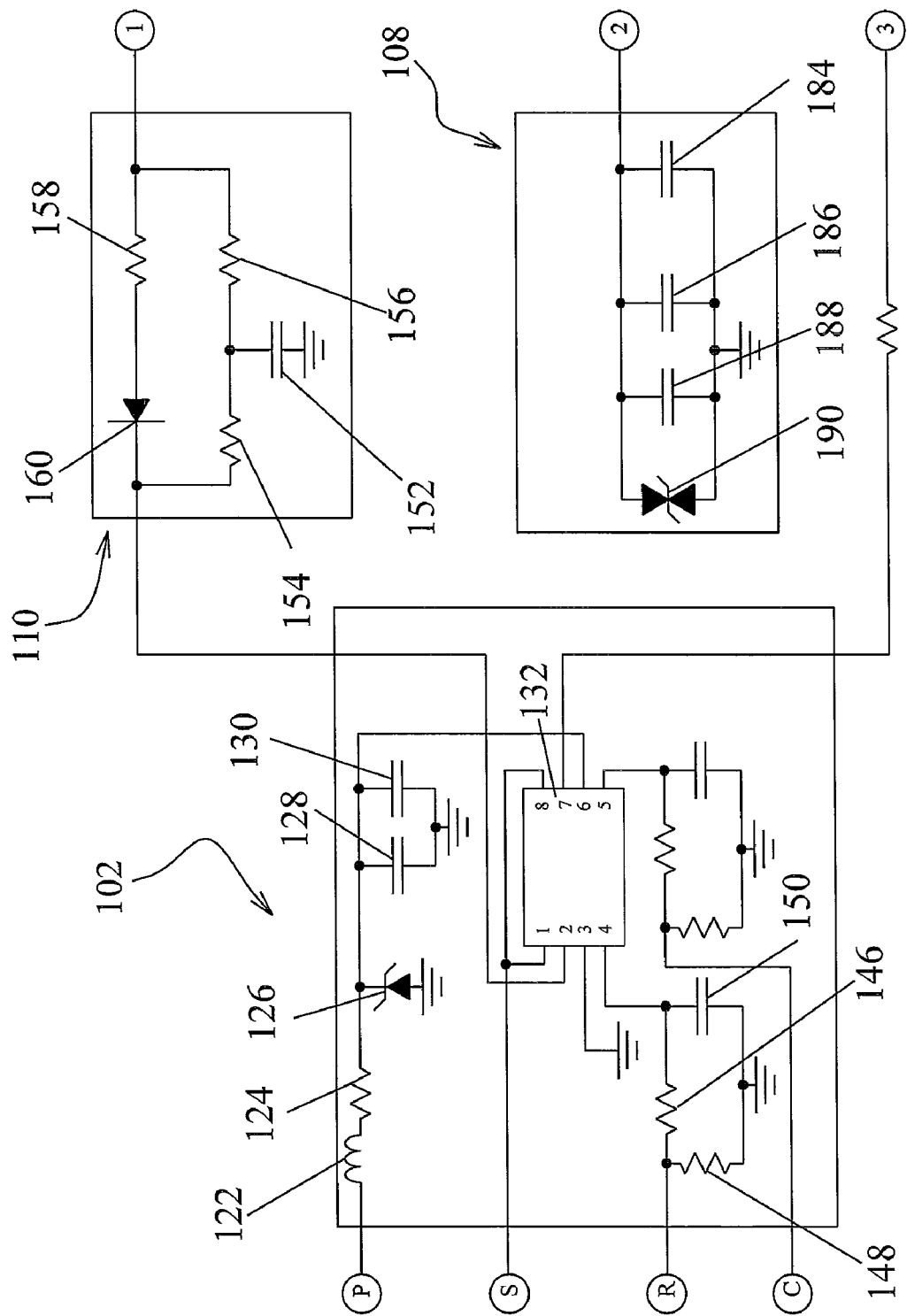
Figure 4B:
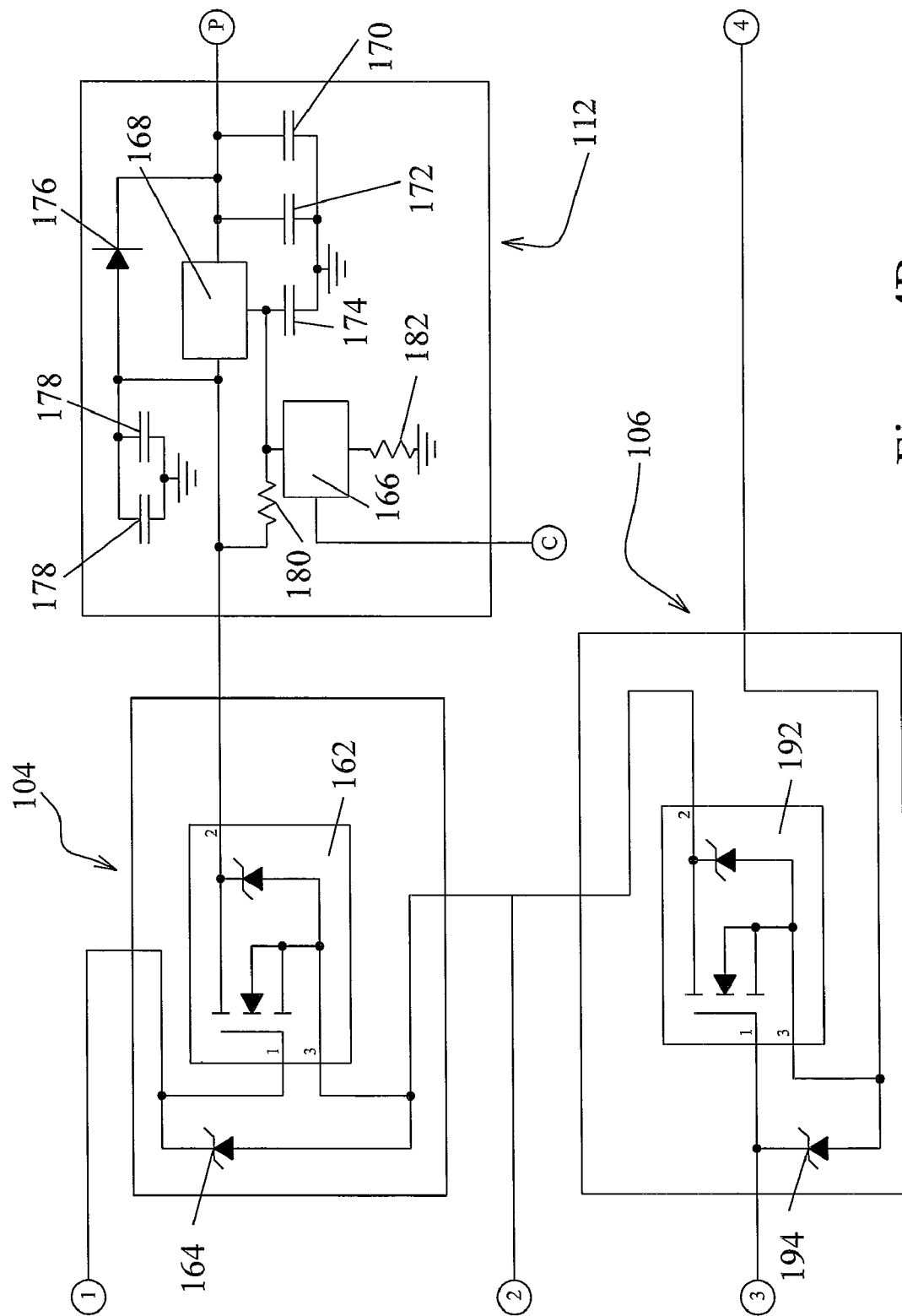
Figure 4C:
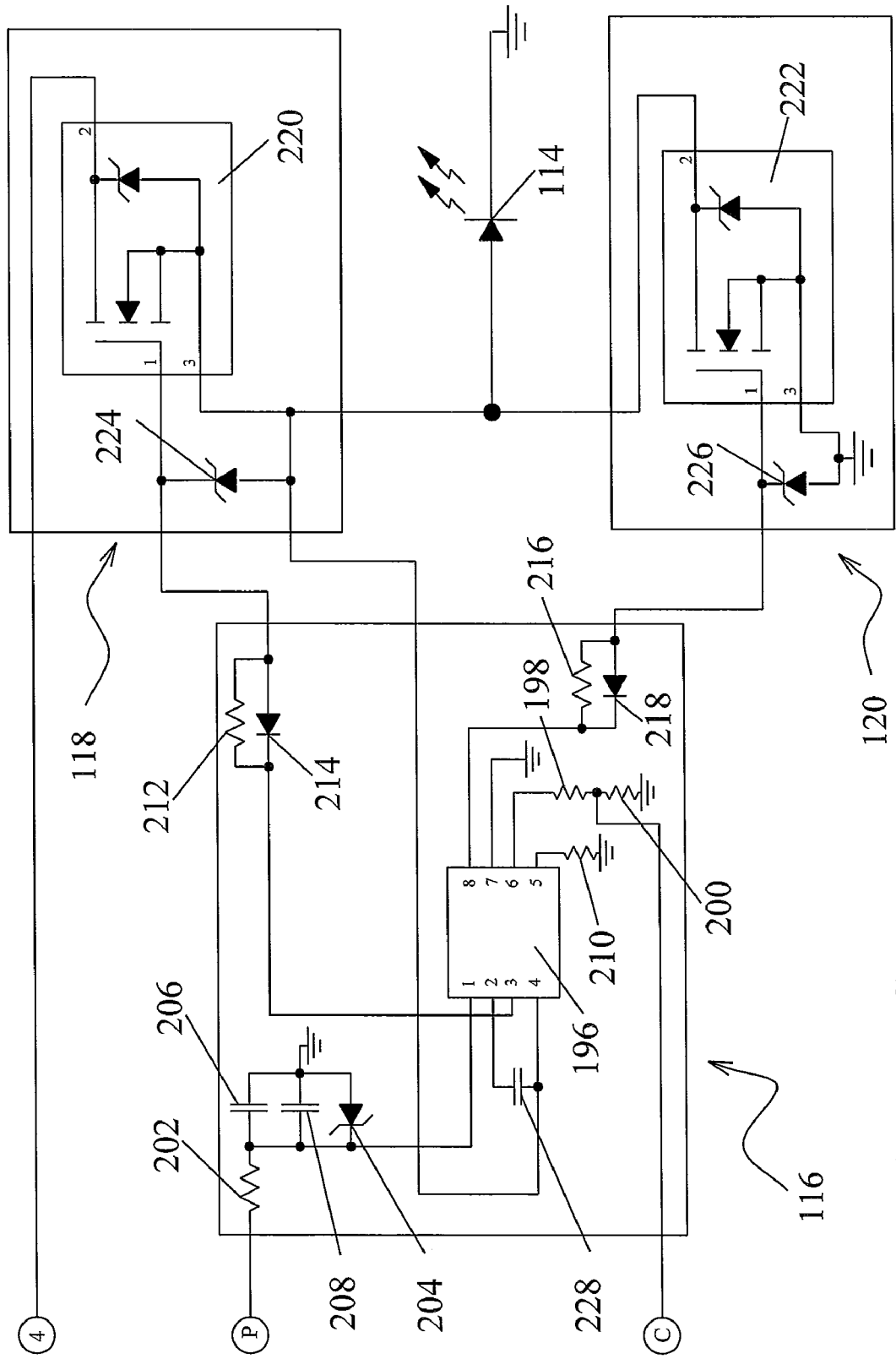
Figure 5:
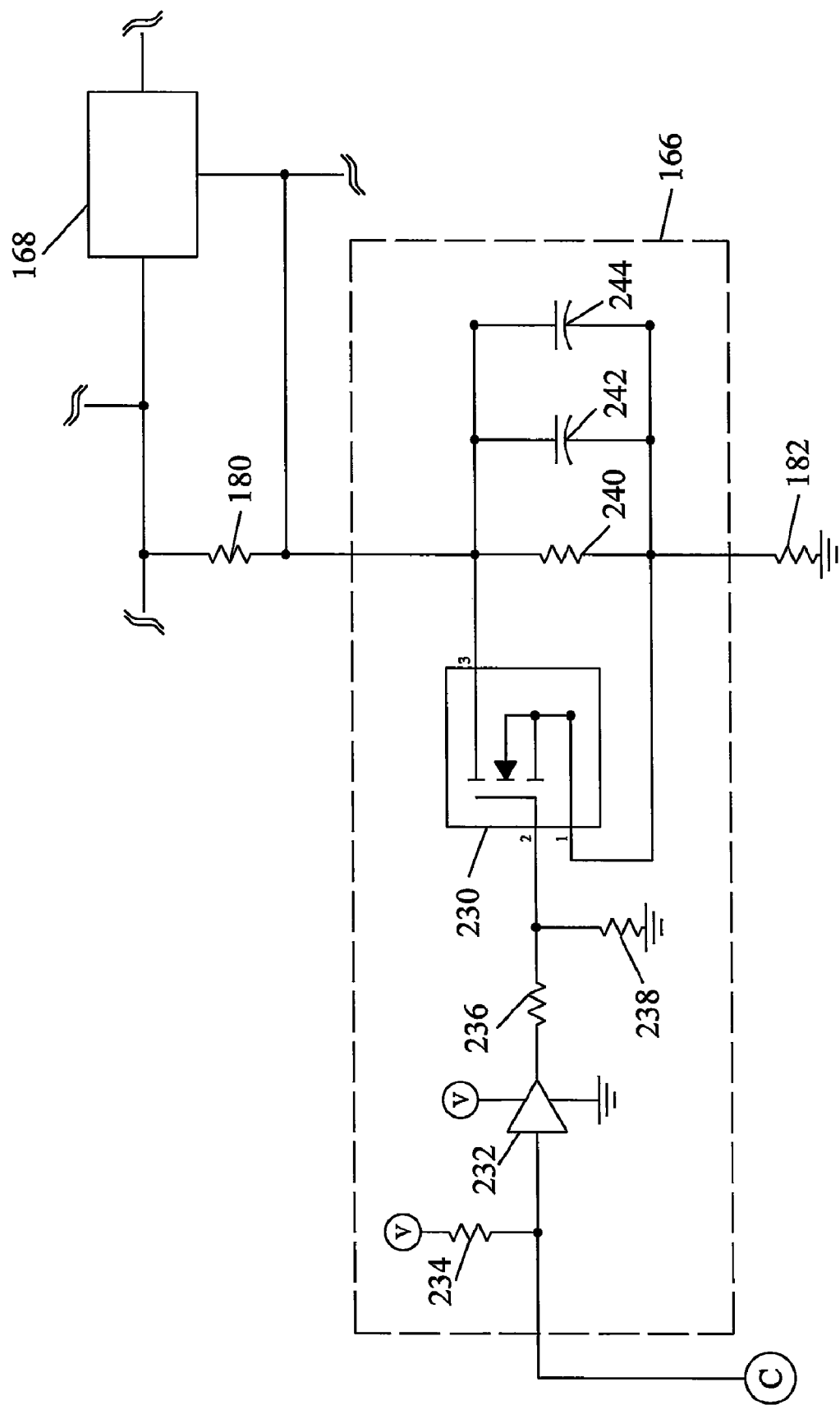
FIG. 5 shows a digitally controlled voltage regulator according to the present invention.

The control circuit 100 is illustrated in greater detail in FIGS. 4A, 4B, and 4C. The switch control unit 102 is connected to a power source at P, preferably 24 V. An inductor 122 provides reverse filtering by preventing high frequency transient electrical signals, produced in the control circuit 100 when the LED device 114 is rapidly switched on and off, from propagating back into other parts of the blood processing apparatus. The incoming voltage is regulated through a resistor 124 and across a Zener diode 126 and capacitors 128, 130, which are connected to ground. One 128 of the capacitors is large enough to smooth fluctuations in the incoming electrical power, while the other capacitor 130 is about two orders of magnitude smaller and presents a path to ground for the high frequency transients blocked by the inductor 122. The regulated voltage is connected to the Vs pin, pin 6, of an integrated switching circuit 132, for example a dual MOSFET driver LTC1255CS8 available from Linear Technology. Pin numbers correspond to the exemplary LTC1255CS8 device. The ground pin, pin 3, of the integrated switching circuit 132, is connected to system ground. The exemplary switching circuit 132 provides two MOSFET switching channels. Such switching channels could be provided by separate integrated circuits or by discrete components. The drain sense pins, pin 1 and pin 8, are both connected to reset circuitry (not shown). Reset circuitry should provide a signal to reset the switching circuit 132 in response to certain conditions such as inadequate voltage, or initial conditions wherein operational delays are introduced to allow initial transients to settle out. The structure of such reset circuitry is known to those of skill in the art and is dependant on the characteristics of the associated microprocessor, and need not be more fully described here. In the switching circuit 132, the gate drive pins, pin 2 and pin 7, are driven to ground when a switch is to be turned off or they are driven high when a switch is turned on. Persons skilled in the art will recognize, of course, that circuits using opposite polarity may also be used. The input pins, pin 4 and pin 5, of the present example are active high and, in the exemplary LTC1255 integrated circuit, should be held low during the application of power to properly set an internal input latch. Input pin 4 is connected through a voltage divider circuit comprising resistors 144, 146, 148 and capacitor 150. A reset circuit (not shown) at connection R keeps input pin 4 low, and the associated MOSFET closed, when adequate power (e.g., 24 V) is not available for an adequate length of time (e.g., longer than 2 seconds). If adequate power is detected, input pin 4 opens gate drive pin 2, and charging of the control circuit 100 begins. Current flows into the charging rate control circuit 110 where a large resistor 154 and capacitor 152 allow the MOSFET to close in a controlled manner and limit the initial rate of current flowing into the capacitor bank 108. It is desirable to manage this inrush of current flow into the capacitor bank to prevent an abrupt increase or spike in current could adversely affect other circuits, such as microprocessors or cause power supply or system resetting. A small resistor 156 (about ⅒ of the large resistor 154) is connected in series with the large resistor 154, the capacitor 152 being connected between the two resistors 154, 156. A return current path is provided through a resistor 158 and diode 160, connected in parallel with the above-mentioned large and small resistors 154, 156 and capacitor 152, and is forward biased to discharge the gate of the MOSFET integrated circuit 162 in the first switch circuit 104.

A signal from the charging rate control circuit 110 closes the first switch circuit 104, allowing current to flow from the voltage control circuit 112 to the capacitor bank 108. The first switch circuit 104 comprises a power MOSFET integrated circuit 162, for example, an IRFZ44N MOSFET available from International Rectifier, which acts as a switch. The gate of the MOSFET 162 is coupled to the gate drive pin 2 of the switching circuit 132 through the charging rate control circuit 110. The source of the MOSFET is connected to the capacitor bank 108 and the second switch circuit 106. The drain of the MOSFET 162 is connected to the voltage control circuit 112. A Zener diode 164 connected across the gate and the source clamps the voltage at the gate to 12 volts.

The voltage control circuit 112 receives instructions to set the voltage on the capacitor bank 108 consistent with the voltage requirements of LED devices driven by the circuit 100. LED devices emitting different wavelengths or colors generally require different voltage levels. The voltage for the particular control circuit 100 is selected by microprocessors controlling the blood processing apparatus through connection C connected to a digital control circuit 166, which will be more fully described below. The digital control circuit 166 controls the adjust pin on an adjustable voltage regulator 168, for example an LT1085CT available from Linear Technology, by changing the voltage at a location between a first resistor 180, which is connected to the out pin of the regulator, and the digital control circuit 166 in series with a second resistor 182, which is connected to system ground. The in pin of the voltage regulator 168 is connected to the 24-volt power supply P. Capacitors 170, 172, and 174 may filter noise and transients from both the power supply P and the digital control circuit 166, providing stability of performance. The out pin of the regulator 168 is connected through the drain of the MOSFET 162 to the capacitor bank 108. The regulated voltage at the out pin is the maximum voltage to which the capacitor bank can be charged. A reverse biased diode 176 may be connected between the out pin of the regulator 168 and the in pin of the regulator to protect the regulator in the event that the capacitor bank is charged, but the connection to the power supply P is interrupted. One or more capacitors 178 may also be connected to the out pin of the regulator whereby high frequency transient voltages may be conducted to ground.

The capacitor bank 108 comprises one or more capacitors 184, 186, 188 connected on one side between the first switch circuit 104 and the second switch circuit 106 and on the other side to system ground. A bi-directional transient voltage suppressor or "back-to-back" Zener diode 190 may be provided in parallel with the capacitors to provide transient protection for the capacitors, particularly if the rated voltage of the capacitors is close to the maximum voltage available from the power supply. Physically smaller capacitors are desirable due to constraints of space in the preferred application. When the first switch circuit 104 is closed, the capacitors 184, 186, 188 are charged to the voltage set by the voltage control circuit 112. When the second switch circuit 106 is closed, the capacitors 184, 186, 188 are connected to further circuit elements and are ready to provide drive current to the LED device, as more fully explained below.

The second switch circuit 106 comprises a power MOSFET integrated circuit 192, for example, an IRFZ44N MOSFET available from International Rectifier, which acts as a switch. The gate of the MOSFET 192 is coupled to gate drive pin 7 of the switching circuit 132 in the switch control unit 102. The drain of the MOSFET is connected to the capacitor bank 108 and the first switch circuit 104. The source of the MOSFET 192 is connected through the first rapid response switch 118 to the LED device 114. A Zener diode 194 connected across the gate and the source clamps the voltage at the gate to 12 volts.

Electric power delivered from the capacitor bank 108 through the second switch circuit 106 to the LED device 114, as connected through first rapid response switch 118, is controlled by the pulse drive controller 116, which selectively opens and closes the first rapid response switch 118 and the second rapid response switch 120, allowing current to flow into and out of LED device 114. The pulse drive controller 116 comprises a half-bridge gate driver 196, such as an LM5104 integrated circuit from National Semiconductor. The gate driver 196 receives signals from the microcomputer C at an input pin 6. A resistor 198 in series with the computer input and the input pin 6 limits the current at the pin. Another resister 200 connected to the computer input and to system ground holds the voltage at the input pin 6 low in the absence of a control pulse from the computer. The VDD or voltage in pin 1 of the gate driver 196 receives electrical power for the gate driver through a voltage regulator comprising a resistor 202 and 12-volt Zener diode 204 connected in series between the power supply P and system ground. One or more capacitors 206, 208 may be connected in parallel with the Zener diode to conduct high frequency transients to ground. The gate driver is grounded through Vss pin 7. A resistor 210 connecting the dead time programming pin 5 to system ground sets a delay between high and low transitions in the gate driver. This delay prevents the gate driver from closing the first rapid response switch 118 and the second rapid response switch at the same time, which would short the capacitor bank to ground. In response to a signal from the computer C, the gate driver 196 produces a signal at high out pin 3. The signal passes through a resistor 212, which damps the turn-on characteristics of the first rapid response switch 118 and controls voltage spikes and generation of radiated electrical interference as the first rapid response switch is closed. The gate of MOSFET 118 may discharge through diode 214 in parallel with resistor 212. As the signal from the computer C ends, the gate driver 196 produces a signal at low out pin 8. This signal also passes through a resistor 216, which damps the turn-on characteristics of the second rapid response switch 120 and controls voltage spikes and generation of radiated electrical interference as the second rapid response switch is closed. The gate of MOSFET 222 may discharge through diode 218 in parallel with resistor 216. The second rapid response switch 120 is normally "on" or "closed", except when a pulse is produced. In contrast, first rapid response switch 118 is normally "off" or "open". Thus, in the exemplary embodiment, when the signal from a microprocessor through C is low, switch 118 is off, while switch 120 is on, and the LED device 114 produces no light. As the signal from the microprocessor through C goes high, both switches 118, 120 are momentarily open or off. As the output at C remains high, switch 118 turns on (closes), while switch 120 stays open or off. The LED device produces light. As the signal from the microprocessor returns to low, both switches 118, 120 are again momentarily open or off. Switch 120 then turns on or closes, and the LED device discharges to ground. One skilled in the art will recognize that the polarity of the signals, the states of the switches, and the direction of current flow through the LED device could be reversed without departing from the teachings of the present invention.

Both the first rapid response switch 118 and the second rapid response switch 120 are comprised of a power MOSFET 220, 222, for example an IRFZ44N MOSFET available from International Rectifier, with a Zener diode 224, 226 connected across the gate and the source of the respective power MOSFET as a voltage clamp for the respective gate of the MOSFET 220, 222. The drain of the MOSFET 220 of the first rapid response switch 118 is connected to the second switch circuit 106, as described above. When the capacitor bank is charged and the second switch circuit 106 is closed, the signal to the gate of the MOSFET 220 from the gate driver 196 causes the MOSFET 220 to conduct power from the MOSFET source through the LED device 114 to ground. The MOSFET source is also connected to a high side MOSFET source connection pin 4 on the gate driver 196. A bootstrap capacitor 228 connects the source connection pin 4 to a bootstrap rail pin 2 of the gate driver 196. When the signal from the computer C ends, the gate driver 196 initially both opens the rapid response switch 118 and leaves the second response switch 120 open for a very brief time (on the order of nanoseconds, as adaptively controlled by gate driver 196), thereby preventing a short circuit from the capacitor bank to system ground. The gate driver 196 then provides a signal to the gate of the MOSFET 222 in the second rapid response switch 120, causing the MOSFET 222 to conduct to system ground. Any power energizing the LED device 114 is conducted away from the LED device to ground. A sharp, well-controlled square-wave voltage, with well-defined leading and trailing edges, can thereby be produced on the LED device, so that the duration and magnitude of illuminations produced by the LED device are consistent.

Preferably, each control circuit 100 controls an LED device or devices of a single type or output frequency. The LED device may produce illumination in the visible or invisible regions of the spectrum, such as red, green or infrared light or full-spectrum white light, as may be appropriate for the desired application. Preferably, two LED devices may be connected in parallel, reducing the cost, size and complexity of the drive circuits. In addition, failure of one of the LED devices would not completely incapacitate a specific control circuit.

The blood processing apparatus described herein and in U.S. Pat. Nos. 7,422,693 and 7,327,443 uses precisely controlled pulses of light to illuminate blood components in the observation region, detect the state of separation of the blood components, and control the operation of the blood processing apparatus. The energy of the pulses is a function both of the duration of the pulses and the amplitude of the pulses. Control of the duration of the pulses was described in U.S. Pat. No. 7,327,443. The amplitude of the pulses can be controlled by regulating the voltage on the capacitor bank 108, which drives the LED light sources. As described in U.S. Pat. No. 7,327,443, a potentiometer may be used as element 166 to control the voltage regulator 168. This is adequate for limited procedures and limited ranges of voltage control. It has been found, however, a wider range of voltage control is needed to accommodate a wide range of blood processing procedures. Distinguishing red blood cells as a primary product, or white blood cells, or plasma, or components of any of them requires different levels of illumination, particularly levels of illumination transmitted through the blood components. This range of voltage control should preferably extend from 3 volts to 22.5 volts with a stability of plus or minus 0.1 volt. Moreover, the control should be temperature independent, and stable over the expected operating temperatures of the blood processing device. Apheresis blood processing centrifuges typically operate for extended periods of time for one or more donors. This often causes temperature variation in the device, particularly increase in operating temperature. The desired control should not be affected by such changes. Moreover, the output of the voltage regulator 168 has a relatively high amperage, so that the capacitor bank can be charged rapidly, as required by the high speed of the centrifuge. These constraints make the digital potentiometer described in U.S. Pat. No. 7,327,443 inadequate over the entire range of performance.

The digital control circuit 166 described herein for controlling the high amperage voltage regulator 168 comprises an N-channel switched mode FET 230. The switched mode FET 230 receives a pulsed digital signal from the microprocessor controlling the blood processing apparatus across line C through a non-inverting buffer 232. A pull-up resister 234 connected to a power source (for example, 5 volts) maintains the incoming signal in the operating range of the buffer 232. The output signal of the buffer 232 is slowed by the RC time constant associated with a resistor 236 and the internal capacitance of the FET 230. An input resistor 238, coupled to the drain of the FET and to ground prevents overload on the FET. A by-pass resistor 240 in parallel with the FET 230 and in series with the resistors 180, 182 described above allows most of the current to flow past the FET, thus avoiding overheating of the FET. The performance of the FET, therefore, remains stable despite extended use of the apparatus.

The pulsed output of the FET 230 is coupled in parallel across a smoothing capacitor 242. In this manner, a selected voltage drop is maintained which is dependent on the switching rate of the FET, but which is seen by the voltage regulator 168 as a constant selected voltage. A high-frequency by-pass capacitor 244, also in parallel with the FET 230, allows spurious high frequency transient signals to be grounded without affecting the voltage presented to the voltage regulator 168.

The control circuit 166 described herein allows for temperature-stable control of the voltage regulator 168 and capacitor bank 108 over a relatively wide range of selected voltages, for example between 3 volts and 22.5 volts. Moreover, the voltage stored on the capacitor bank 108 can be precisely controlled within 0.1 volts or less despite high amperage output from the voltage regulator 168 to the capacitor bank 108, thus allowing precise control of the LED light sources over a wide range of power levels. These features allow the blood processing apparatus to be programmed for numerous blood processing procedures without re-calibrating the LED light sources. Moreover, automated calibration and diagnostics by digital control of programmed pulse generation can be provided when the apparatus is coupled with optical feedback in the system. Photo sensors may be provided in conjunction with the LED light sources, such that the output of the light sources are measured by the photo sensors. Increments of the voltage stored on the capacitor bank can then be correlated to changes in detected light intensity.

I claim:
1. A centrifuge blood processing system for separating blood components comprising
 a separation chamber rotating about a central axis, said separation chamber having an observation region;
 a stroboscopic light source illuminating at least said observation region;

a camera receiving images of said observation region as illuminated by said stroboscopic light source;

an intensity control apparatus in electrical communication with said light source, said intensity control apparatus having at least one capacitor coupled to said light source, a linear voltage regulator coupled to and periodically charging said capacitor, and means for digitally controlling the output voltage of said linear voltage regulator, said means for digitally controlling said output voltage comprising a switched mode field effect transistor (FET).

2. The centrifuge blood processing system of claim 1 wherein said stroboscopic light source comprises a plurality of light emitting diodes (LED).

3. The centrifuge blood processing system of claim 1 further comprising a microprocessor and means for controlling said switched mode FET with a pulsed digital signal from said microprocessor.

4. The centrifuge blood processing system of claim 1 further comprising a by-pass resistor in parallel with the FET.

5. The centrifuge blood processing system of claim 4 further comprising a smoothing capacitor connected to said FET, said smoothing capacitor converting pulsed output of said FET into a stable output for controlling said linear voltage regulator.

6. The centrifuge blood processing system of claim 1 further comprising a high-frequency by-pass capacitor coupled to said FET.

7. A centrifuge blood processing system for separating blood components comprising a separation chamber rotating about a central axis, said separation chamber having an observation region;

a stroboscopic light source illuminating at least said observation region;

a camera receiving images of said observation region as illuminated by said stroboscopic light source;

an intensity control apparatus in electrical communication with said light source, said intensity control apparatus having at least one capacitor coupled to said light source, a linear voltage regulator coupled to and periodically charging said capacitor, and a digital control circuit controlling the output voltage of said linear voltage regulator, wherein said digital control circuit comprises a switched mode field effect transistor (FET).

8. The centrifuge blood processing system of claim 7 wherein said stroboscopic light source comprises a plurality of light emitting diodes (LED).

9. The centrifuge blood system of claim 7 further comprising a microprocessor controlling the blood processing apparatus and wherein said switched mode FET receives a pulsed digital signal from said microprocessor.

10. The centrifuge blood processing system of claim 7 further comprising a by-pass resistor in parallel with the FET.

11. The centrifuge blood processing system of claim 7 further comprising a smoothing capacitor connected to said FET, said smoothing capacitor converting pulsed output of said FET into a stable output for controlling said linear voltage regulator.

12. The centrifuge blood processing system of claim 7 further comprising a high-frequency by-pass capacitor coupled to said FET.

13. The centrifuge blood processing system of claim 7 wherein said digital circuit for controlling the output voltage comprises means for digitally controlling voltage delivered to said light source up to at least 22.5 volts in increments of 0.1 volts or less.

14. The centrifuge blood processing system of claim 13 further comprising a plurality of light sources of different frequencies and a plurality of means for digitally controlling voltage, each of said light sources of different frequency being controlled by a separate means for digitally controlling voltage.

15. The centrifuge blood processing system of claim 14 wherein said stroboscopic light source comprises a plurality of light emitting diodes (LED).

16. A centrifuge blood processing system for separating blood components comprising a separation chamber rotating about a central axis, said separation chamber having an observation region;

a stroboscopic light source illuminating at least said observation region;

a camera receiving images of said observation region as illuminated by said stroboscopic light source;

means for controlling voltage delivered to said stroboscopic light source, said means for controlling voltage being temperature independent, and stable over the expected operating temperatures of the blood processing device.

17. The centrifuge blood processing system of claim 16 wherein said stroboscopic light source comprises a plurality of light emitting diodes (LED).

* * * * *